United States Patent [19]

Tiger

[11] 4,150,671
[45] Apr. 24, 1979

[54] WARM AIR WEATHERMASK

[76] Inventor: Howard L. Tiger, Eagle Ridge Way, West Orange, N.J. 07054

[21] Appl. No.: 770,106

[22] Filed: Feb. 18, 1977

[51] Int. Cl.² ............................................. A61M 15/00
[52] U.S. Cl. .................................. 128/212; 128/146.5; 128/146.6
[58] Field of Search .................... 128/212, 188, 191 R, 128/195, 192, 205, 142 R, 146 R, 146.3, 140 N

[56] References Cited

U.S. PATENT DOCUMENTS

| 1,999,086 | 4/1935 | Claudius | 128/191 R |
| 3,326,214 | 6/1967 | McCoy | 128/212 |
| 3,895,675 | 7/1975 | Rein et al. | 128/212 |
| 4,007,737 | 2/1977 | Paluch | 128/188 |

FOREIGN PATENT DOCUMENTS

| 210601 | 6/1907 | Fed. Rep. of Germany | 128/212 |
| 1364599 | 5/1964 | France | 128/212 |

Primary Examiner—Henry J. Recla
Attorney, Agent, or Firm—Charles E. Baxley

[57] ABSTRACT

This disclosure teaches an apparatus in the form of a face mask which in addition to protecting the face from direct impingement of cold air, snow, sleet and the like, also serves to preheat air prior to inspiration thereof by indirect heat exchange against warm exhaled air. Illustratively, an intake conduit having heat exchanging fins is mounted concentrically within an exhaust conduit, all within a face-fitting housing. Warm, exhaled air transfers its heat to incoming air.

9 Claims, 3 Drawing Figures

WARM AIR WEATHERMASK

BACKGROUND OF THE INVENTION

There is a need in the art for comfortable, convenient and inexpensive means for prewarming air for breathing. For example, in the case of persons suffering from cardiac insufficiency, whether congenital or acquired as a result of heart damage resulting from injury or disease, the patient is commonly advised to engage in moderate exercise, as tolerated. One of the best of such exercises is walking, which is of course normally an outdoor activity. This, however, may lead to problems, particularly in cold weather. Under cold conditions, the heart is doubly stressed—partially by the physical demand on the muscles, requiring increased circulation to carry away lactic acid and other waste products of muscular activity, and partially by the additional increased circulation required to maintain the body temperature at a proper level. The latter stress does not signal its presence by muscular discomfort, as does the former, and the result is that the patient is unconsciously placing greater demands on his heart than he should. The same effect is commonly experienced by persons having no previous history of cardiac problems, as one is reminded every year by an upswing in incidence of heart attacks which can be directly associated with heavy exercise such as snow shovelling during periods of cold weather. One of the most direct mechanisms whereby the body is chilled is by inhalation of cold air which not only chills the tissues forming the walls of the components of the respiratory tract, but also chills the bloodstream itself by heat transfer which takes place in the alveole concurrently with the oxygenation of oxygen-depleted blood from the pulmonary artery. Thus, the demands placed on the heart for maintenance of body temperature can be alleviated and the above-mentioned problems can be overcome to an appreciable degree, by preheating air before it is inspired into the body.

Previous attempts to solve this problem have generally taken the form of interposing a porous barrier, for example of knit wool or spongy polymer, between the nose and/or mouth of the user and the external atmosphere. While successful to a degree, such measures suffer from certain disadvantages. For example, the interposed porous material necessarily involves some resistance to free air flow, and to that extent makes breathing more difficult. Also, there is an annoying tendency for mositure in exhaled breath to condense on contact with the cold ambient atmosphere, and to deposit as moisture or as ice crystals on the surface and in the pores of the porous material, creating a most uncomfortable condition. Perhaps more importantly, the mechanism whereby the warming of incoming air is accomplished is by direct heat exchange with warm exhaled air in the porous material. This necessitates that a certain amount of the exhaled air be trapped in the porous material, mixed with fresh incoming air to accomplish the desired heat exchange, and then reinhaled as part of the mixture. This, in turn, defeats pro tanto the advantage of the heat exchange, inasmuch as the mixture being breathed has already been partially depleted of oxygen, so that additional quantities of the mixed gases must be inhaled in order to maintain the required oxygen supply.

OBJECTS OF THE INVENTION

An object of the invention, therefore, is to provide an improved face-protective weathermask.

A further object is to provide an improved weathermask comprising means for preheating incoming air on its way to the user's respiratory tract.

Another object is to provide such a weathermask, which avoids the necessity of interposing porous material in the path of incoming air and of exhaled air.

still another object is to provide such a weathermask, which overcomes the tendency of moisture in exhaled air to condense on contact with cold incoming air, thereby further impeding free air flow and creating an umcomfortable condition conducive to chapping and the like.

Yet another object is to provide a mask of the type described, which avoids the necessity of mixing exhaled air with fresh incoming air in order to effect the necessary heat exchange, and the concomitant necessity of rebreathing a portion of the exhaled air.

Other objects, advantages and uses of the invention will be apparent to those skilled in the art from the following more complete description and claims, and the accompanying drawings.

BRIEF STATEMENT OF THE INVENTION

The foregoing objects are accomplished according to the present invention, which contemplates apparatus for preconditioning air to be breathed by a user of said apparatus, said apparatus comprising in combination:

an intake conduit defined by an enclosed tube having a distal end communicating with a source of breathable, oxygen-containing gas and a proximal end communicating with the respiratory tract of the user, said intake conduit being operative to convey said oxygen-containing gas from said source to said respiratory tract, means associated with said intake conduit for preventing substantial reverse flow of gas from said respiratory tract toward said source, an exhaust conduit comprising an enclosed tube having a distal end communicating with an appropriate receiver for gases exhausted from said respiratory tract and a proximal end communicating with the respiratory tract of said user, said exhaust conduit being operative to convey said gases exhausted from said respiratory tract to said receiver, and means associated with said exhaust conduit for preventing substantial reverse flow from said receiver toward said respiratory tract, said intake conduit and said exhaust conduit being juxtaposed in indirect heat-exchange relationship.

BRIEF DESCRIPTION OF THE DRAWINGS

This invention, and the foregoing objects, features and advantages will appear more fully from the accompanying drawings, viewed in conjunction with a detailed description of preferred embodiments of the invention, taken together with the appended claims. In the drawings, in which the same numerals refer to like elements throughout:

DESCRIPTION OF PREFERRED EMBODIMENTS

Figure 2:
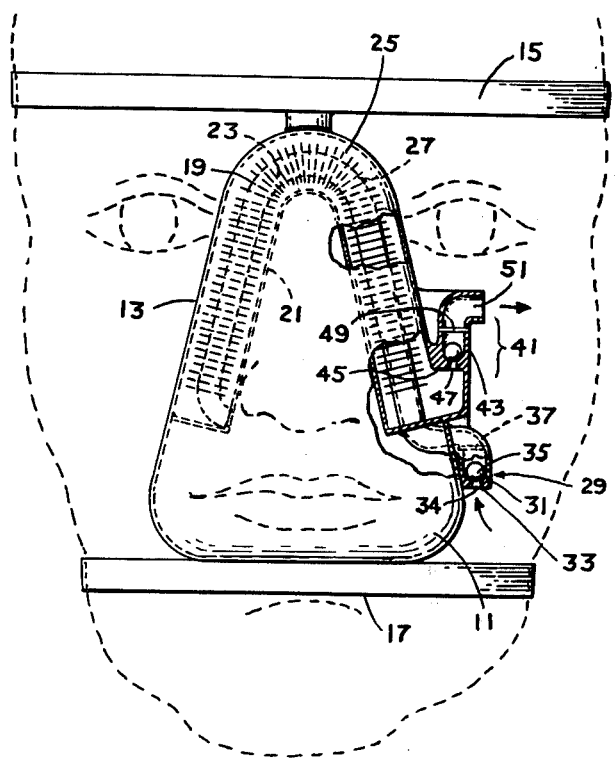
FIG. 2 is a front elevation similar to FIG. 1, with parts broken away to show internal details of construction.

Referring to the drawings, and particularly FIG. 2, the apparatus according to the invention comprises a housing 11 having a periphery 13 contoured to fit closely against the face of the wearer in such a way as to cover both the nose and the mouth of the wearer, leaving the eyes uncovered. Obviously, other conformations may be selected, e.g. such as to cover only the nose or only the mouth (while preferably sealing off the mouth or the nose, respectively, to prevent inspiration of air which has not previously been conditioned by passage through the apparatus), or the housing may be extended to cover the eyes as well, including a transparent area for vision. The illustrated form of housing, however, has been found preferable in most applications for maximum comfort and efficiency.

The housing 11 may be held in position against the face of the user in any convenient manner, as by elastic straps 15 and 17.

The wall of housing 11 is interrupted to provide an aperture or apertures for passage of the distal ends of tubes 19 and 21, respectively defining the distal ends of intake conduit 23 and exhaust conduit 25.

Inside housing 11 are two concentric tubes 19 and 21, tube 19 being disposed internally of tube 21. The center bore of tube 19 forms the major part of intake conduit 23, and the annular space between the exterior surface of tube 19 and the interior surface of tube 21 forms the major part of exhaust conduit 25.

Figure 1:
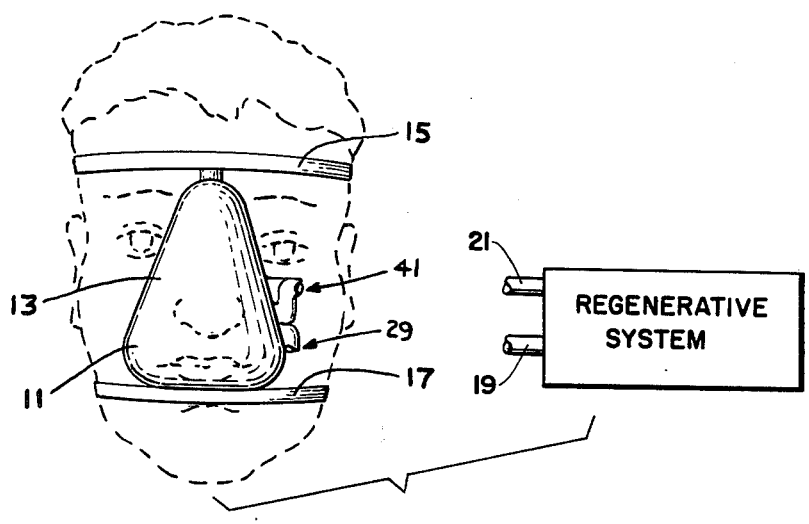
FIG. 1 is a front elevation showing the mask of this invention mounted in position on the face of a user.
Figure 3:
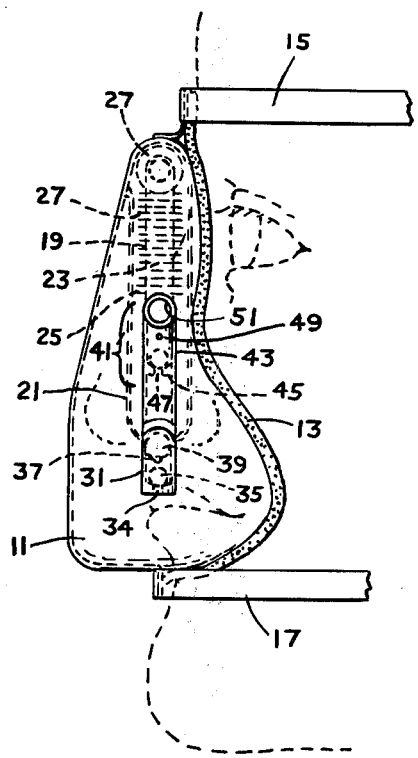
FIG. 3 is a side elevation, partly in section, of the apparatus as shown in FIGS. 1 and 2.

The concentric tubes 19 and 21 may be led in the general form of an inverted V along the sides and across the bridge of the nose as illustrated in FIGS. 1 and 3, with the advantage of helping to keep the sides of the nose and adjacent portions of the cheeks warm, and also lessening net loss of heat through the outer wall of tube 21. Alternatively, the concentric tubes may be routed otherwise, for example across the mouth, as will be obvious to those skilled in the art.

The proximal ends of the concentric tubes 19 and 21 both open into the face mask. If desired, the inner tube 19 may project beyond the end of tube 21, to minimize short-circuiting and may even, if so desired, be prolonged, positioned and shaped to provide a mouthpiece so that by inhaling through the mouth and exhaling through the nostrils, the user may avoid short-circuiting altogether. Resort to this extreme, however, is ordinarily neither necessary nor desirable; the comfort of the user is better served by simply terminating both tubes within the housing 11, and the short-circuiting problem is sufficiently taken care of by the system of check valves hereinafter described.

To improve the efficiency of heat transfer between the warm exhaled air in exhaust conduit 23 and incoming air to be warmed thereby in intake conduit 21, the outer surface of tube 19 is preferably provided with fins 27 projecting from said surface into the annular space constituting conduit 25.

To provide an orderly, unidirectional flow to the gases, flow-controlling means are provided in the form of check valves. Valve 29, associated with tube 19 forming the major part of intake conduit 23, may be placed at any desired point in intake conduit 23 but preferably and most conveniently at the distal end of tube 19. As illustrated in FIGS. 2 and 3, valve 29 comprises a generally vertical cylindrical housing 31 closed at its lower end by a disc-shaped bottom 33 perforated by a central intake orifice 34, and containing a light-weight sphere 35 of a size to ride loosely up and down in said housing and to block intake orifice 34 at the lower end of its travel. The housing is also provided with a retaining member 37 to prevent escape of the sphere 35, and communicates, either at its top or through a side orifice 39 with the intake or distal end of tube 19.

In operation, a slight negative pressure in tube 19 permits the outside atmospheric pressure to lift the sphere 35 away from intake orifice 34 permitting air to enter through said orifice into said housing and thence flow into and through tube 19 to the interior of housing 11. conversely, a slight positive pressure in tube 19 operates to seal sphere 35 against intake orifice 34, preventing egress of gases through said intake orifice.

In similar manner, exhaust valve 41 is preferably disposed adjacent the distal end of exhaust 21, and comprises housing 43, bottom 45 perforated to define an exhaust orifice 47, retaining member 49, and an offtake 51 communicating with the atmosphere. Exhaust valve 41 operates on a principle similar to that of intake valve 29, to prevent intake of air into the system through exhaust orifice 47. The net result is that during inhalation, prewarmed air is withdrawn from intake conduit 23 into the respiratory tract of the user and replaced in the conduit by fresh air entering through intake orifice 34 where it is preheated by indirect heat transfer against previously-exhaled air in exhaust conduit 25. Upon exhalation the internal pressure is increased, allowing heat-depleted, previously-exhaled air to be exhausted from exhaust conduit 25 through exhaust orifice 47 and replaced in said exhaust conduit by warm, freshly-exhaled air.

Other forms of check valve, such as flap valves, split diaphragms, etc. may obviously be substituted for the ball-checks illustrated, as will be apparent to those skilled in the art.

By the use of the apparatus as described, the function of preheating cold air for breathing is readily, conveniently, efficiently and inexpensively accomplished, while avoiding the aforementioned disadvantages of the prior art.

It will be noted that whenever in the present description, an element is described as being in communication with the respiratory tract of the user, it is understood that a direct connection of such element to the internal portions of the respiratory tract is not necessarily nor ordinarily implied; such element is to be considered to communicate with the respiratory tract if it communicates with one or more of the external portions thereof—i.e. the mouth and/or the nosrils.

The apparatus according to this invention may also be used for other purposes in addition to its primary prupose of prewarming cold air prior to breathing the same. Such other purposes normally employ other apparatus elements, known per se, in conjunction with the apparatus according to the present invention, and will be merely suggested, rather than describing each of them in detail.

One of such additional functions is the use of compressed gas tanks for the supply of breathable gas, for example pure oxygen for therapeutic purposes, or compressed mixtures, for example of oxygen and helium, as sometimes used for underwater breathing apparatus. Another is the introduction of controlled amounts of vaporous medication into the atmosphere to be breathed.

Another of such ancillary uses is the collection of samples of exhaled breath for analysis and/or diagnostic tests.

Still another is the connection of both the intake and exhaust orifices with appropriate parts of a regenerative system, for the purpose of removing waste products from exhaled air and replenishing its oxygen content to reclaim a breathable oxygen-containing gas. Such an application is particularly suitable for use in a vacuum or in other hostile environments, such as created by the presence of noxious gases.

While this invention has been described in terms of certain preferred embodiments and illustrated by way of certain drawings, these are illustrative only, and the invention is not to be construed as limited, except as set forth in the appended claims.

I claim:

1. Apparatus for preconditioning air to be breathed by a user of said apparatus, said apparatus comprising in combination:

housing means having a periphery contoured to fit closely against the user's face, an intake conduit defined by an enclosed tube within the housing, the tube having a distal end communicating with a source of breathable, oxygen-containing gas and breathing means at its proximal end for communicating with the respiratory tract of the user, said intake conduit being operative to convey said oxygen-containing gas from said source to said respiratory tract, means associated with said intake conduit for preventing substantial reverse flow of gas from said respiratory tract toward said source, an exhaust conduit comprising an enclosed tube within the housing, the tube enclosing a portion of the intake conduit, the intake conduit being essentially concentric therewithin, an appropriate receiver, the exhaust conduit having a distal end communicating with said appropriate receiver for gases exhausted from said respiratory tract and a proximal end communicating with said breathing means communicating with the respiratory tract of said user, said exhaust conduit being operative to convey said gases exhausted from said respiratory tract to said receiver, and means associated with said exhaust conduit for preventing substantial reverse flow of gas from said receiver toward said respiratory tract, said intake conduit and said exhaust conduit being juxtaposed in indirect heat-exchange relationship wherein said conduits are disposed adjacent said periphery of said housing means to be closely adjacent to the face of the user, thereby improving heat conservation in the system comprising said apparatus and said face, and minimizing loss of heat from said system to the ambient atmosphere.

2. Apparatus according to claim 1, wherein said intake conduit and said exhaust conduit are juxtaposed in counter-current indirect heat exchange relationship.

3. Apparatus according to claim 1, wherein the distal end of said exhaust conduit communicates with the ambient atmosphere, said atmosphere thereby constituting said receiver for gases exhausted from said respiratory tract.

4. Apparatus according to claim 1, wherein said distal end of said intake conduit communicates with the ambient atmosphere, said atmosphere thereby constituting said source of breathable, oxygen-containing gas.

5. Apparatus according to claim 1, wherein said respective distal ends of said intake conduit and said exhaust conduit communicate with the ambient atmosphere, said atmosphere thereby constituting said source of breathable, oxygen containing gas and said receiver for gases exhausted from said respiratory tract.

6. Apparatus according to claim 1, wherein said respective distal ends of said intake conduit and said exhaust conduit communicate with a regenerative system for conversion of said gases exhausted from said respiratory tract to a breathable, oxygen-containing gas mixture.

7. Apparatus according to claim 1, wherein both of said tubes are of circular cross-section and said inner tube is disposed internally of and concentric with said outer tube.

8. Apparatus according to claim 1, wherein said intake conduit is defined by the internal bore of said inner tube and said exhaust conduit is defined by the space between the outer face of said inner tube and the inner face of said outer tube.

9. Apparatus according to claim 1, wherein said inner tube is finned to facilitate indirect heat exchange between said conduits.

* * * * *